(12) United States Patent
Miao et al.

(10) Patent No.: US 11,704,798 B2
(45) Date of Patent: Jul. 18, 2023

(54) METHOD AND DEVICE FOR VERTEBRA LOCALIZATION AND IDENTIFICATION

(71) Applicant: Ping An Technology (Shenzhen) Co., Ltd., Shenzhen (CN)

(72) Inventors: Shun Miao, Bethesda, MD (US); Fakai Wang, Bethesda, MD (US); Kang Zheng, Bethesda, MD (US); Le Lu, Bethesda, MD (US)

(73) Assignee: PING AN TECHNOLOGY (SHENZHEN) CO., LTD., Shenzhen (CN)

(*) Notice: Subject to any disclaimer, the term of this patent is extended or adjusted under 35 U.S.C. 154(b) by 308 days.

(21) Appl. No.: 17/212,428

(22) Filed: Mar. 25, 2021

(65) Prior Publication Data

US 2022/0172350 A1    Jun. 2, 2022

Related U.S. Application Data

(60) Provisional application No. 63/120,693, filed on Dec. 2, 2020.

(51) Int. Cl.
  *G06T 7/00* (2017.01)
  *G16H 50/20* (2018.01)

(52) U.S. Cl.
  CPC .......... *G06T 7/0012* (2013.01); *G16H 50/20* (2018.01); *G06T 2207/10028* (2013.01); *G06T 2207/20081* (2013.01); *G06T 2207/20084* (2013.01); *G06T 2207/30012* (2013.01)

(58) Field of Classification Search
  CPC ......... G06T 7/0012; G06T 2207/10028; G06T 2207/20081; G06T 2207/20084; G06T 2207/30012; G06T 2207/10081; G06T 7/73; G16H 50/20; G16H 30/40; G06V 10/46; G06V 20/647; G06V 30/18057; G06V 2201/033
  See application file for complete search history.

(56) References Cited

U.S. PATENT DOCUMENTS

2016/0210740 A1* 7/2016 Ma ............................ G06T 7/10
2018/0260951 A1* 9/2018 Yang ....................... G06N 3/084

OTHER PUBLICATIONS

Hao Chen, Chiyao Shen, Jing Qin, Dong Ni, Lin Shi, Jack C.Y. Cheng, and Pheng-Ann Heng: "Automatic Localization and Identification of Vertebrae in Spine CT via a Joint Learning Model with Deep Neural Networks"; In MICCAI 2015, pp. 515-522. (Year: 2015).*

* cited by examiner

*Primary Examiner* — Siamak Harandi
(74) *Attorney, Agent, or Firm* — Anova Law Group, PLLC

(57) ABSTRACT

A vertebra localization and identification method includes: receiving one or more images of vertebrae of a spine; applying a machine learning model on the one or more images to generate three-dimensional (3-D) vertebra activation maps of detected vertebra centers; performing a spine rectification process on the 3-D vertebra activation maps to convert each 3-D vertebra activation map into a corresponding one-dimensional (1-D) vertebra activation signal; performing an anatomically-constrained optimization process on each 1-D vertebra activation signal to localize and identify each vertebra center in the one or more images; and outputting the one or more images, wherein on each of the one or more outputted images, a location and an identification of each vertebra center are specified.

20 Claims, 9 Drawing Sheets

Algorithm 1: Optimization

Input: $Q_{v=1,\ldots,26}(z)$ and $\hat{Q}(z)$
$v_l \leftarrow 1$ ;
$\mathbf{k} \leftarrow$ the coordinates of local maxima of $\hat{Q}(z)$ ;
$\mathcal{L}_{min} \leftarrow \infty$ ;
while *true* do
    $v_l \leftarrow \arg\min_{v_l} \mathcal{L}(v_l, \mathbf{k})$    // offset ;
    if $\mathcal{L}(v_l, \mathbf{k}) < \mathcal{L}_{min}$ then
        | $\mathcal{L}_{min} \leftarrow \mathcal{L}(v_l, \mathbf{k})$ ;
    else
        | return $(v_l, \mathbf{k})$ associated with the lowest $\mathcal{L}$ ;
    end
    $\mathbf{k} \leftarrow \arg\min_{\mathbf{k}} \mathcal{L}(v_l, \mathbf{k})$    // fine-tune ;
    $u \leftarrow \arg\min_{u \in [0, N-2]} \mathcal{L}(v_l, E(\mathbf{k}, u))$ ;
    $\mathbf{k} \leftarrow E(\mathbf{k}, u)$    // expansion ;
end
Result: $(v_l, N, \mathbf{k})$

FIG. 4

METHOD AND DEVICE FOR VERTEBRA LOCALIZATION AND IDENTIFICATION

CROSS-REFERENCE TO RELATED APPLICATION

This application claims the priority of U.S. Provisional Patent Application No. 63/120,693, filed on Dec. 2, 2020, the entire content of which is incorporated herein by reference.

FIELD OF THE TECHNOLOGY

This application relates to the field of medical image interpretation and, more particularly, to a method and device for vertebra localization and identification.

BACKGROUND OF THE DISCLOSURE

Accurate localization and identification of spine vertebrae in three-dimensional (3-D) medical images are important for computer-aided diagnosis of spine disorders. Due to similar appearances of the spine vertebrae, it is difficult to identify the vertebrae with a substantially high accuracy. Various existing approaches take advantages of machine learning algorithms to improve the accuracy. However, those approaches are ineffective in incorporating anatomical constraints in the computer-aided diagnosis.

Thus, there is a need to provide method, device, and storage medium for vertebra localization and identification, to effectively utilize the anatomical knowledge to achieve best accuracy and robustness.

SUMMARY

One aspect of the present disclosure includes a vertebra localization and identification method. The method includes: receiving one or more images of vertebrae of a spine; applying a machine learning model on the one or more images to generate three-dimensional (3-D) vertebra activation maps $\{G_v\}$ of detected vertebra centers; performing a spine rectification process on the 3-D vertebra activation maps $\{G_v\}$ to convert each 3-D vertebra activation map $G_v$ into a corresponding one-dimensional (1-D) vertebra activation signal $Q_v$; performing an anatomically-constrained optimization process on each 1-D vertebra activation signal $Q_v$ to localize and identify each vertebra center in the one or more images; and outputting the one or more images, wherein on each of the one or more outputted images, a location k and an identification $v_l$ of each vertebra center are specified, wherein $v_l \in [1, 26]$.

Another aspect of the present disclosure includes a vertebra localization and identification device. The device includes a memory storing a computer program and a processor configured to execute the computer program stored in the memory to: receive one or more images of vertebrae of a spine; apply a machine learning model on the one or more images to generate three-dimensional (3-D) vertebra activation maps $\{G_v\}$ of detected vertebra centers; perform a spine rectification process on the 3-D vertebra activation maps $\{G_v\}$ to convert each 3-D vertebra activation map $G_v$ into a corresponding one-dimensional (1-D) vertebra activation signal $Q_v$; perform an anatomically-constrained optimization process on each 1-D vertebra activation signal $Q_v$ to localize and identify each vertebra center in the one or more images; and output the one or more images, wherein on each of the one or more outputted images, a location k and an identification $v_l$ of each vertebra center are specified, wherein $v_l \in [1, 26]$.

Another aspect of the present disclosure includes a non-transitory computer-readable storage medium storing a computer program. When being executed by a processor, the computer program performs: receiving one or more images of vertebrae of a spine; applying a machine learning model on the one or more images to generate three-dimensional (3-D) vertebra activation maps $\{G_v\}$ of detected vertebra centers; performing a spine rectification process on the 3-D vertebra activation maps $\{G_v\}$ to convert each 3-D vertebra activation map $G_v$ into a corresponding one-dimensional (1-D) vertebra activation signal $Q_v$; performing an anatomically-constrained optimization process on each 1-D vertebra activation signal $Q_v$ to localize and identify each vertebra center in the one or more images; and outputting the one or more images, wherein on each of the one or more outputted images, a location k and an identification $v_l$ of each vertebra center are specified, wherein $v_l \in [1, 26]$.

Other aspects of the present disclosure can be understood by those skilled in the art in light of the description, the claims, and the drawings of the present disclosure.

BRIEF DESCRIPTION OF THE DRAWINGS

FIG. 4 illustrates an exemplary pseudo code of an optimization process consistent with embodiments of the present disclosure;

DETAILED DESCRIPTION

Figure 1:
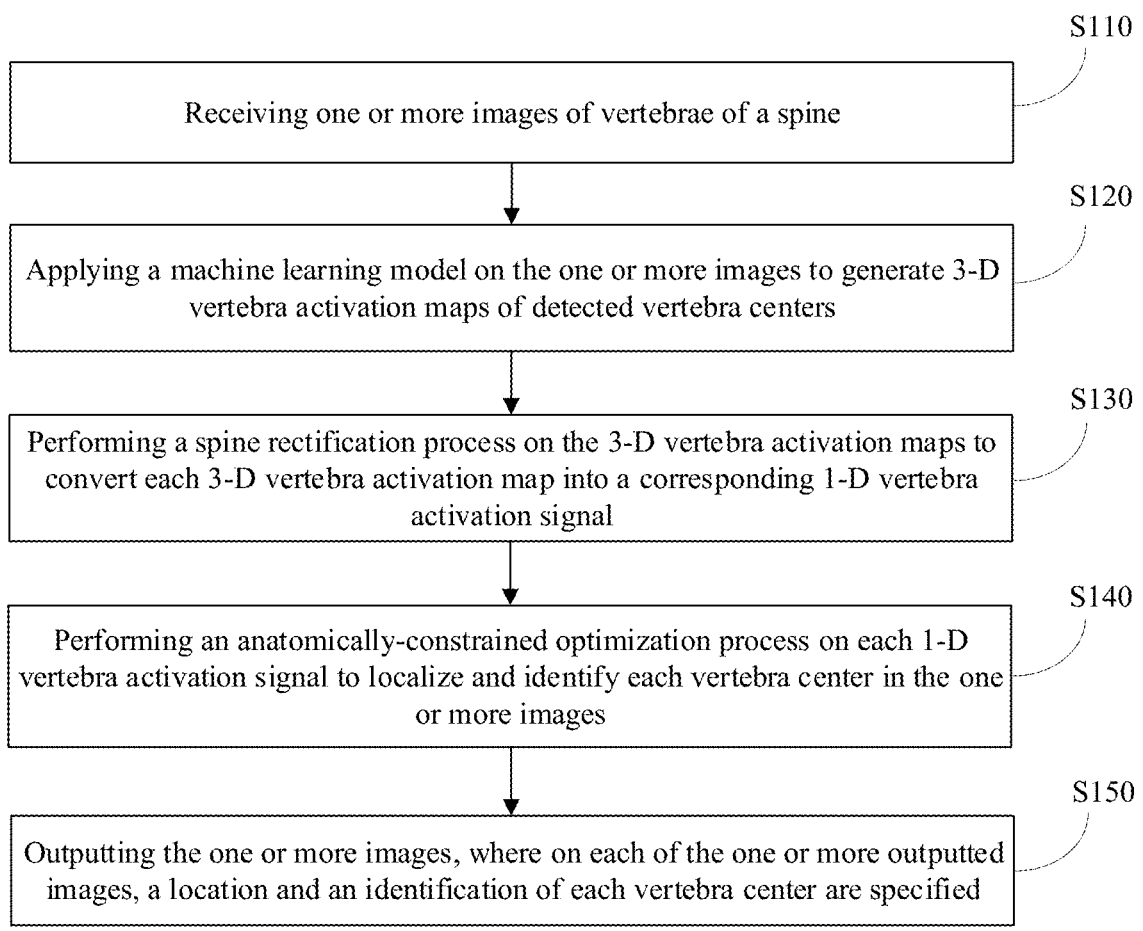
FIG. 1 illustrates a flowchart of an exemplary method for vertebra localization and identification consistent with embodiments of the present disclosure.

The following describes the technical solutions in the embodiments of the present invention with reference to the accompanying drawings. Wherever possible, the same reference numbers will be used throughout the drawings to refer to the same or like parts. Apparently, the described embodiments are merely some but not all the embodiments of the present invention. Other embodiments obtained by a person skilled in the art based on the embodiments of the present invention without creative efforts shall fall within the protection scope of the present disclosure. Certain terms used in this disclosure are first explained in the followings.

Bidirectional recurrent neural networks (Bi-RNN): Bi-RNN connect two hidden layers opposite directions to the same output. With this form of generative deep learning, the output layer can get information from past (backward) and future (forward) states simultaneously.

Spine images: spine images are usually Computed tomography (CT) images. A CT scan is a medical imaging technique that uses computer-processed combinations of multiple X-ray measurements taken from different angles to produce tomographic (cross-sectional) images of a body or a section of the body, allowing a user to see inside the body without cutting.

Convolutional neural network (CNN): a CNN includes an input layer that performs the activation function, hidden layers that perform convolutions, and an output layer that performs the final convolution. The hidden layers do multiplication or other dot product. The activation function is commonly ReLU. CNN is a class of deep neural networks, most commonly applied to analyzing visual imagery.

Fully convolutional network (FCN): FCN is an architecture employing solely locally connected layers, such as convolution, pooling, and up-sampling. Avoiding the use of dense layers means less parameters and makes the networks faster to train.

Stochastic gradient descent (SGD): SGD is an iterative method for optimizing an objective function with suitable smoothness properties.

U-Net: it is a convolutional neural network for biomedical image segmentation. The network is based on the fully convolutional network and its architecture was modified and extended to work with fewer training images and to yield more precise segmentations.

Vertebrae: 26 vertebrae in the human vertebral column are divided into different regions corresponding to the curves of the spinal column. Vertebrae in these regions are essentially alike, with minor variation. These regions are called the cervical spine, thoracic spine, lumbar spine, sacrum, and coccyx. There are seven cervical vertebrae (C1-C7), twelve thoracic vertebrae (T1-T12), and five lumbar vertebrae (L1-L5).

To distinguish spine vertebrae with similar shapes and appearances, various existing approaches attempted to address this issue by exploiting anatomical prior knowledge including a spatial order of the spine vertebrae and a distance between neighboring spine vertebrae. In one example, spine anatomical knowledge is incorporated into neural networks implicitly using Bi-RNN or explicitly using an information aggregation layer considering the spatial distribution prior knowledge of the spine vertebrae. In another example, the anatomical prior knowledge has been used to post-process neural network outputs. In these examples, the anatomical prior knowledge is not fully utilized. In particular, anatomy-inspired network architectures like Bi-RNN rely on the network to learn the anatomical prior knowledge without the guaranteed respect to the prior knowledge. Building the anatomical prior knowledge into a network layer or an optimization target makes a compromise that turns a hard constraint (e.g., the spatial order, which should be strictly enforced) into a soft constraint that can be violated. As a result, the existing approaches sometimes produce physically implausible predictions (e.g., vertebrae in reversed order, multiple occurrences of a same vertebra.)

When the existing approaches employ information exchange mechanisms (e.g., Bi-RNN and message passing) to bring a global context into vertebra label classification scores, each vertebra label is still classified individually at the output stage without imposing anatomical constraints. Thus, the existing approaches completely depend on the information exchange mechanisms to capture and regulate the spatial relationships between different spine vertebrae. Existing fusion mechanisms include Bi-RNN and aggregation of neighboring vertebrae activation maps following the vertebrae distance prior knowledge. The Bi-RNN encourages the massage passing between different spine vertebrae in a softly learned way instead of enforcing it in an anatomy coherent manner. The aggregation of the neighboring vertebrae activation maps is only reliable for short-range relationships, leaving the global anatomical prior knowledge insufficiently exploited.

In another example, a specific optimization formulation is used to jointly label the spine vertebrae by formulating a global objective function. However, Markov modeling of vertebra labels is limited to capture the short-range relationships and errors accumulate with each Markov step.

The present disclosure provides a vertebra localization and identification method that jointly labels all vertebrae with the anatomical constraints to effectively utilize the anatomical prior knowledge and achieve best accuracy and robustness. Specifically, a key point localization U-Net model is trained to predict three-dimensional (3-D) activation maps for 26 vertebra centers. Along an automatically calculated spine centerline, the 3-D activation maps are warped to rectify the spine and aggregated to form one-dimensional (1-D) vertebra activation signals. An optimization process is then performed on the 1-D vertebra activation signals by incorporating a hard constraint of the spatial order of the spine vertebrae to limit an optimization search space (also referred to as a constraint search space) and a soft constraint of the prior knowledge of distances between the spine vertebrae (i.e., a regularization term in an objective function.) Labels of all spine vertebrae are searched jointly in the constraint search space, which allows global message passing among the spine vertebrae and ensures the anatomical plausibility of results.

Figure 2:
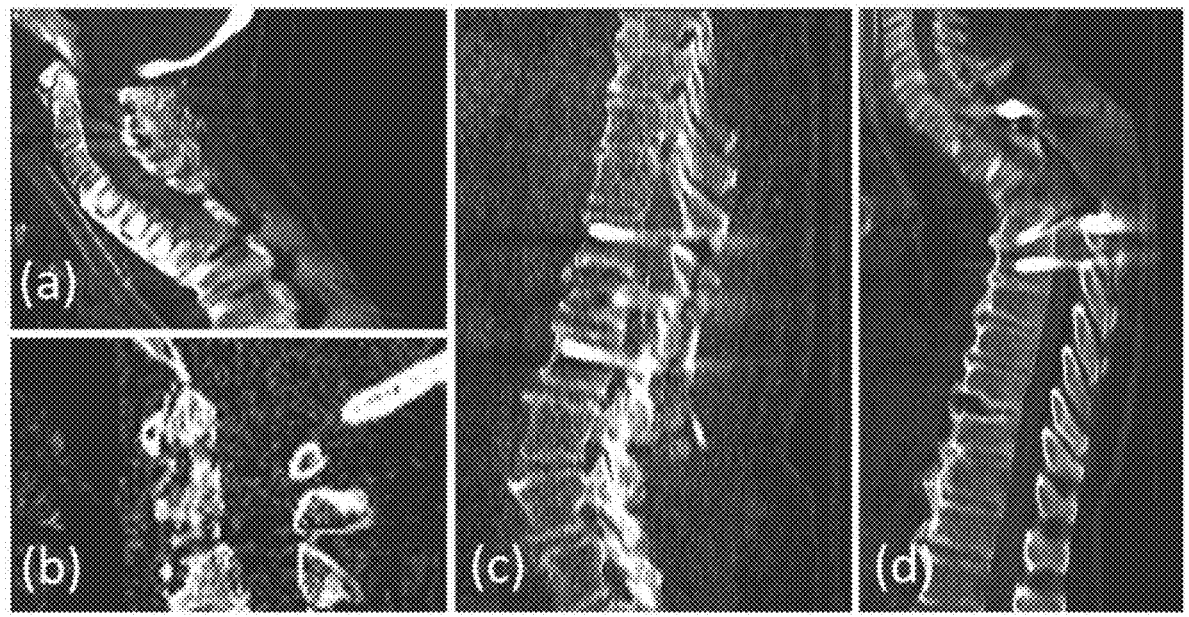
FIG. 2 illustrates exemplary spine images consistent with embodiments of the present disclosure.

The vertebra localization and identification method consistent with the present disclosure is evaluated based on publicly available benchmarks (e.g., SpineWeb). Training datasets for the method include 242 CT images and testing datasets for the method include 60 CT images. FIG. 2 illustrates exemplary spine CT images. As shown in FIG. 2, some CT images have a small field of view (a), a low image quality (b), and metal implants and severe compression fractures (c, d). The disclosed method achieves an identification rate of 97.4%, substantially outperforming the best existing method that achieves the identification rate of 94.7%.

The vertebra localization and identification method consistent with the present disclosure aggregates 3-D vertebra activation maps into 1-D vertebra activation signals to substantially reduce optimization complexity, exploits the spatial order of the spine vertebrae as the hard constraint of the optimization search space to anatomically ensure plausible results, and includes the vertebra distance prior knowledge as the soft constraint in the objective function, thereby improving the identification rate from 94.7% to 97.4% and cutting an error rate by half.

Before the era of deep learning, the vertebra localization and identification relied on hand-crafted low-level image features and/or priori knowledge. Regression forests and probabilistic graphical models are often used to handle the CT images of arbitrary field-of-view. Sparse centroid annotations are further transformed into dense probabilistic labels for classifier training. A hierarchical strategy is used to learn detectors dedicated to distinctive vertebrae and non-distinctive vertebrae. However, the above approaches produce erroneous results on challenging pathological images due to the limited modeling power of hand-crafted features. In addition, these approaches fail to exploit global contextual information to facilitate vertebra identification.

Employing deep neural networks to detect spine vertebrae has achieved substantially improved performance. In one example, the deep neural networks such as convolutional neural network (CNN) and fully convolution network (FCN) have been employed to directly detect the vertebra centers and achieve the vertebra localization and identification jointly in one stage. In another example, multi-stage approaches have been employed to locate and identify the spine vertebrae, which can be categorized into top-down or bottom-up strategies. The top-down strategy locates the whole spine first and detects individual vertebrae next while the bottom-up strategy first detects the landmarks of all vertebrae and then classifies them into respective vertebrae.

The prior knowledge of spine anatomy has been used to facilitate the vertebra localization and identification. Specifically, domain expert knowledge is used to categorize vertebrae into anchor and bundle sets which are treated differently in the process. Markov modeling is adopted to label the spine vertebrae by preserving a consecutive order. In some cases, the anatomical knowledge is learned automatically in a data-driven manner. For example, Bi-RNN is used to enable a machine learning model to capture the spatial relationships of predictions in different spine regions, and a message passing mechanism is used to exploit prior distribution of the distances between the spine vertebrae to regulate the prediction. Adversarial learning has also been employed to encode and impose the anatomical prior knowledge. The multi-stage approaches may embed the knowledge of the spine anatomy in the top-down and bottom-up representations.

FIG. 1 illustrates a flowchart of an exemplary method for vertebra localization and identification consistent with embodiments of the present disclosure. As shown in FIG. 1, one or more images of vertebrae of a spine is received (S110). Specifically, the one or more images of size W×H×L are denoted as I, where W, H, and L are a size of the CT images, $I \in \mathbb{R}^{W \times H \times L}$, and $\mathbb{R}$ is a mathematical expression of real numbers. The goal of the vertebra localization and identification is to detect centers of vertebrae that are present in I and to identify their labels. Each of the detected vertebrae is indexed by V, where $V \subseteq \{1, 2, \ldots, 26\}$. The centers of the detected vertebrae are labeled as C1-C7 in a cervical vertebra region, T1-T12 in a thoracic vertebra region, L1-L5 in a lumbar vertebra region, and S1-S2 in a sacrum vertebra region.

At S120, a machine learning model is applied on the one or more images to generate 3-D vertebra activation maps of detected vertebra centers. Specifically, the machine learning model takes the one or more images I as input and outputs vertebra center annotations $P=\{x_v, y_v, z_v\}$, where P is 3D coordinates of the vertebra centers in the original CT images, and $v \in V$. In one embodiment, the machine learning model is a U-Net key point detection model. The U-Net key point detection model is trained by a training dataset of CT images, in which the vertebra center annotations P are provided. In another embodiment, another suitable machine learning model may be used to generate the 3-D vertebra activation maps of the detected vertebra centers.

Figure 3:
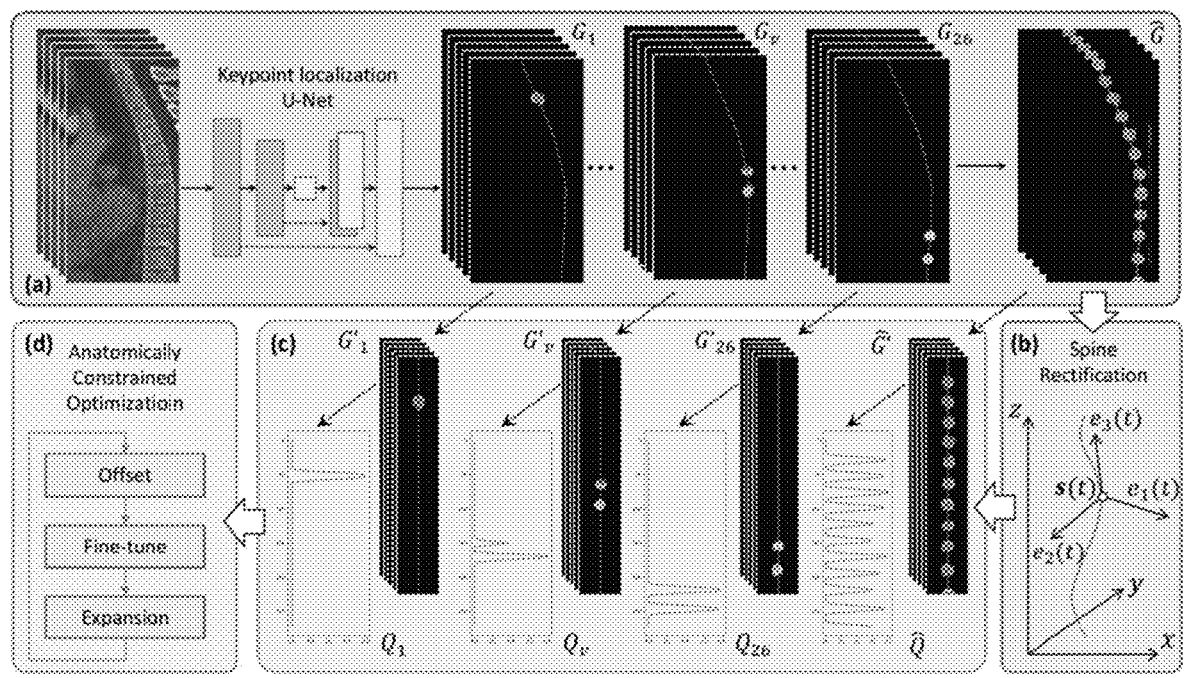
FIG. 3 illustrates an exemplary method for vertebra localization and identification consistent with embodiments of the present disclosure.

In one embodiment, the U-Net key point detection model is trained to produce the 3-D activation maps of the detected vertebra centers. The U-Net key point detection model is trained using a widely adopted multi-channel activation map regression approach. The multi-channel ground-truth activation maps are generated using Gaussian distribution centered on the spatial coordinates of the vertebra centers. The U-Net key point detection model is trained using L2 loss on the predicted and ground-truth activation maps. The produced 3-D vertebra activation maps are denoted as $\{G_v\}$, where $G_v \in \mathbb{R}^{W \times H \times L}$, and $v \in V$. Although each activation map channel is trained to activate around the center of the corresponding vertebra, due to the repetitive visual patterns of vertebrae, it is not uncommon for the heap map to falsely activate on a wrong vertebra or activate on multiple vertebrae, as shown in FIG. 3(a).

In a standard key point detection (or localization) method, each activation map channel predicted by the machine learning model is individually processed by taking the pixel with maximum activation or taking a centroid to obtain the key point detection results. In the embodiments of the present disclosure, instead of directly processing the activation map channels to obtain the vertebra centers, anatomical knowledge is incorporated in the processing to achieve robust and accurate vertebra localization and identification.

Referring to FIG. 1, at S130, a spine rectification process is performed on the 3-D vertebra activation maps to convert each 3-D vertebra activation map into a corresponding one-dimensional (1-D) vertebra activation signal. Specifically, after the 3-D vertebra activation maps are generated, a spine centerline is extracted and each 3-D vertebra activation map is aggregated along the centerline to produce the 1-D vertebra activation signal.

In one embodiment, the activation maps for 26 individual vertebrae are combined into a combined activation map $\hat{G}$ below:

$$\hat{G} = \Sigma_{v=1}^{26} G_v. \quad (1)$$

The above equation represents the probability of any vertebra center without differentiating their indices. While the individual activation map often falsely activates on a wrong vertebra due to repetitive image pattern, the activations are typically only around vertebra centers. Thus, by combining them into one, the centers of all vertebrae are activated, as shown in FIG. 3(a).

In one embodiment, the spine centerline is computed from the combined activation map $\hat{G}$. It is extracted by tracing mass centers of the axial slices of $\hat{G}$, calculated as the average coordinates of pixels with activation above 0.5. The spine centerline is denoted as s(t), where s(t)=(x(t), y(t), z(t)), x(t), y(t), z(t) are coordinates of the centerline s(t), and t is arc-length parameterization including a distance from a starting point of the centerline s(t). Given the spine centerline s(t), the 3-D vertebra activation maps $\{G_v\}$ are warped so that the spine centerline s(t) becomes straight after warping. Specifically, a moving local coordinate system is calculated along the spine centerline and is denoted as $\langle e_1(t), e_2(t), e_3(t) \rangle$, where $e_3(t)$ is a tangent vector of the spine centerline s(t), $e_2(t)$ is a unit vector in the normal plane of the spine centerline s(t) with a minimum angle to a y-axis of the image (i.e., a patient's front direction), and $e_1(t)$ is a cross product of $e_2(t)$ and $e_3(t)$.

The axes $e_1(t)$ and $e_2(t)$ span the normal plane of the spine centerline s(t), where $e_1(t)$ points at a patient's anterior direction and $e_2(t)$ points at a patient's right direction. Given the spine centerline and the local coordinate systems, spine rectified vertebra activation maps $G'_v$ and $\hat{G}'$ are produced by warping $G_v$ and $\hat{G}$ as follows:

$$G'_v(x,y,z) = G_v(s(z) + e_1(x) + e_2(y)), \quad (2)$$

where $G_v(s(z)+e_1(x)+e_2(y))$ denotes linear interpolation of $G_v$ at the given coordinate. The warping operation can be seen as resampling $G_v$ in the normal plane of the spine centerline s(t). In the spine rectified vertebra activation maps, the spine centerline s(t) is straight along z-axis, as shown in FIG. 3(c). The anterior and right directions of each vertebra are aligned with x-axis and y-axis.

The spine rectified activation maps $G'_v$ and $\hat{G}'$ are further processed to produce 1-D vertebra activation signals, denoted as $Q'_v$ and $\hat{Q}'$, respectively. Specifically, values in $G'_v$ are summed along the x-axis and the y-axis, written as $$Q_v(z) = \Sigma_{x,y} G'_v(x,y,z). \quad (3)$$

Since the vertebra activation map is aggregated in the normal plane of the spine centerline, the produced 1-D vertebra activation signal indicates the likelihood of the vertebra center at given location z on the spine centerline. Aggregating the activations in the normal plane strengths the activation signal of the vertebra centers and reducing the spine localization search space to the 1-D substantially simplifies searching complexity, thereby making it possible and affordable to adopt more complex optimization approaches. Despite the strengthened activation, false activations in the original activation map are carried over to the 1-D activation signal, resulting in false activations in the 1-D activation signal, as shown in FIG. 3(c).

Referring to FIG. 1, at S140, an anatomically-constrained optimization process is performed on each 1-D vertebra activation signal to localize and identify each vertebra center in the one or more images. Specifically, the vertebra centers are localized and identified based on the 1-D vertebra activation signals $\{Q_v\}$ and $\hat{Q}'$ by solving an optimization problem. Denoting N as the number of detected vertebrae and $v_l$ as the lowest index among them, since the detected vertebrae must be consecutive, their indices can be represented by $[v_l, v_l+N-1]$. The locations of the detected vertebrae are denoted as $k=\{k_i\}_{i\in[0,N-1]}$, where i is the vertebra's index relative to $v_l$. Thus, $k_i$ indicates the z-axis location of the vertebra with absolute index $v_l+i$. Since N can be represented by k, N is dropped from the parameters for the sake of notation simplicity. The parameters $(v_l, k)$ are optimized to minimize the following energy function:

$$\mathcal{L}(v_l,k) = -\Sigma_{i=0}^{N-1} \lambda_{v_l+i} Q_{v_l+i}(k_i) + \Sigma_{i=2}^{N-2} R(k_i - k_{i-1}, k_{i+1} - k_i). \quad (4)$$

$Q_{v_l+i}(k_i)$ is the activation value of the vertebra with the absolute index $v = v_l+i$. $R(\bullet,\bullet)$ is a regularization term that encourages the distances between neighboring vertebrae to be similar, and can be written as:

$$R(a,b) = \exp\left(\max\left(\frac{a}{b}, \frac{b}{a}\right)\right). \quad (5)$$

$\lambda_v$ denotes weights of the 26 vertebrae. The two vertebrae at both ends of the spine (i.e., C1: cervical-1, C2: cervical-2, S1: the first sacrum, and S2: the last sacrum) are designated as anchors and their weights $\lambda_v$ are set to 2. For all other vertebrae, the weights are set to 1. The vertebrae (C1, C2, S1, and S2) at both ends of the spine have more distinct appearances, and hence are given more weights than others.

In one embodiment, the vertebra centers are jointly searched to maximize the total vertebra activation score while keeping the distances between the vertebra centers regulated. The search space of $(v_l, k)$ implicitly imposes a hard constraint that the detected vertebrae must be consecutive with the indices from $v_l$ to $v_l+N-1$.

In one embodiment, the optimization process performed at S140 includes an initialization step followed by iterative updates. The parameters $(v_l, k)$ are searched in the space: $v_l \in [1,26]$, and $k_i \in [0, L]$. L is a total length of the spine. At the initialization step, $v_l$ is set to 1 and the vertebra centers k are set to the coordinates of local maxima of $\hat{Q}$ sequentially (i.e., $k_{i+1} > k_i$). After the initialization, three operations including a first operation, a second operation, and a third operation are iteratively applied to search the parameters.

The first operation is an offset operation, in which $v_l$ is optimized via exhaustive search:

$$v_l \leftarrow \underset{v_l}{\operatorname{argmin}} \mathcal{L}(v_l, k). \quad (6)$$

The second operation is a fine-tune operation, in which $\{k_v\}$ is optimized via Hill Climbing optimization:

$$k \leftarrow \underset{k}{\operatorname{argmin}} \mathcal{L}(v_l, k). \quad (7)$$

The fine-tune operation adjusts the vertebra centers to minimize the total energy concerning both the individual activation signal $Q_v$ and the distance regularization.

The third operation is an expansion operation, in which a new vertebra center is inserted to k between (u, u+1). Specifically, the expanded k is denoted as E(k, u):

$$k \leftarrow E(k,u) = \begin{cases} k_i & \text{if } i \leq u \\ (k_i + k_{i+1})/2 & \text{if } i = u+1. \\ k_{i+1} & \text{if } i > u \end{cases} \quad (8)$$

The insertion location u is searched by minimizing the energy function below:

$$u = \arg\min_{u \in [0, N-2]} \mathcal{L}(v_l, E(k,u)). \quad (9)$$

The expansion operation addresses missed vertebrae that are not captured by the local maxima of $\hat{Q}$.

The three operations are iteratively applied until the energy function starts to increase (i.e., indicating convergence), that is, $\mathcal{L}_j(v_l, k) > \mathcal{L}_{j-1}(v_l, k)$, where $\mathcal{L}_{j-1}(v_l, k)$ and $\mathcal{L}_j(v_l, k)$ are the energy functions after the (j−1)-th and the j-th iteration of the offset operation, respectively.

Referring to FIG. 1, at S150, one or more images are outputted with each vertebra center localized and each vertebra label identified. Specifically, the parameters $(v_l, k)$ associated with lowest $\mathcal{L}$ during the process are taken as the optimization output. After the vertebra centers are localized from the 1-D vertebra activation signals, the coordinates of the vertebra centers are mapped back to the one or more images following a reverse spatial mapping of the spine rectification to produce final 3-D localization results. Outputting the one or more images may include displaying the one or more images on a screen, printing the one or more images by a printer, transmitting the one or more images to a remote device via a communication network, or storing the one or more images in a storage device for future viewing.

The pseudo code of the optimization process is shown in FIG. 4.

To evaluate the performance of the vertebra localization and identification method consistent with the present disclosure, 302 CT images with vertebra center annotations are obtained from the publicly available benchmarks. The CT images are representative for the vertebra localization and identification tasks due to various pathologies and imaging conditions that include severe scoliosis, vertebral fractures, metal implants, and small field-of-view (FOV). The 302 CT images are split into a training dataset of 242 CT images and a testing dataset of 60 CT images.

Commonly used evaluation metrics for vertebra localization and identification tasks include an identification rate and a localization error. The identification rate measures the percentage of vertebrae that are correctly identified. A vertebra is considered as correctly identified if the detected vertebra center and the ground truth are mutually the closest and their distance is within 20 mm. The localization error measures the mean and standard deviation of localization errors (in mm) of correctly identified vertebrae. The evaluation metrics are calculated for the vertebrae overall, as well as separately for different spine regions (i.e., cervical, thoracic, and lumbar regions.)

In one embodiment, the vertebra localization and identification method is implemented in PyTorch and is executed by a computer workstation. The key point detection model is implemented using nnU-Net. The CT images are re-sampled to 0.3×0.3×1.25 mm spacing. In a training stage, the 3-D patches of size 128×160×64 voxels are cropped from each CT image as input. In an inference stage, the trained key point detection model is applied on non-overlapping patches of the same size to obtain the localized vertebra activation maps for the entire CT image. A stochastic gradient descent (SGD) optimizer with a learning rate of 0.01, a weight decay of 3e−5, and a mini-batch size of 2 are used to train the key point detection model for 1,000 epochs.

The vertebra localization and identification method consistent with the present disclosure is applied on the test dataset of 60 CT images. In the cervical region, the mean error 2.40 mm, the standard deviation 1.18 mm, and the identification rate 96.8% are provided. In the thoracic region, the mean error 2.35 mm, the standard deviation 1.28 mm, and the identification rate 97.8% are provided. In the lumbar region, the mean error 3.19 mm, the standard deviation 1.69 mm, and the identification rate 97.2% are provided. In all regions, the mean error 2.55 mm, the standard deviation 1.40 mm, and the identification rate 97.4% are provided.

Nine baseline methods are selected to compare with the disclosed method. The nine baseline methods include a classic method with hand-crafted feature, techniques with data-driven anatomical prior, and methods with anatomy inspired architectures. While the disclosed method reports the identification rate 97.4% and the mean error 2.55 mm, the closest competing method reports the identification rate 94.7% and the mean error 2.56 mm. An identification error rate is significantly reduced approximately from 5.3% to 2.6%, by absolute 2.7% (or relative 50.9%). When evaluated on three spine regions separately, the identification rates of the disclosed method are still better than all comparison methods, except for the lumbar region when compared to one of the nine baseline methods. On cervical and thoracic spines, the disclosed method achieves the highest identification rates of 96.8% and 97.8%, respectively. Overall, the disclosed method substantially outperforms the nine baseline methods.

The baseline method that outperforms other baseline methods in the identification rate imposes the hard physical constraint by Markov modeling, which ensures the output to be anatomically plausible. Despite the performance gain, the baseline method has a noticeable tendency to achieve higher identification rate in the lumbar region but lower identification rate in the cervical region. Because the baseline method employs Markov modeling to trace vertebrae from one end of the spine (i.e., lumbar) to the other end (i.e., cervical). The Markov modeling successfully regulates the consecutive vertebra indices, which leads to significant performance gain compared to the other baseline methods without such regulation. However, the error accumulates along with the number of Markov steps as the process moves toward the cervical end. In contrast, the disclosed method globally searches and identifies the vertebrae with the constraint of consecutive vertebra indices, which eliminates the directional bias caused by Markov modeling and results in consistent performance in all spine regions.

Further, effects and behavior of the spine rectification and anatomically constrained optimization are analyzed via an ablation study of alternative methods. The most naïve alternative to the iterative optimization is to take the maximum location of individual 3-D activation map $G_v$ as the center of the v-th vertebra, denoted as base model. A slightly more sophisticated approach is to take the maximum location of individual 1-D activation signal $Q_v$ as the center of the v-th vertebra. Since this approach employs the spine rectification, it is denoted as base+rectify model. In the above two approaches, since there is no constraint applied, physically implausible vertebra orders that violate the anatomy can be produced. A more advanced variation is to take the locations of local maximums of $\hat{Q}$ as candidates of consecutive vertebrae and to determine $v_l$ following the equation (6). This approach ensures the consecutive order of the predicted vertebrae on top of the spine rectification, and is thus referred to as base+rectify+order model. This approach is equivalent to the disclosed method that stops after the offset operation in the first optimization iteration. Since the disclosed method employs both the spine rectification and the anatomically constrained optimization, it is referred to as base+rectify+optim model. The results of the ablation study are summarized in Table 1.

TABLE 1

| Model | Cervical | | | Thoracic | | | Lumbar | | | All | | |
|---|---|---|---|---|---|---|---|---|---|---|---|---|
| | Mean error | Std | Id rate | Mean error | Std | Id rate | Mean error | Std | Id rate | Mean error | Std | Id rate |
| base | 2.24 | 1.25 | 96.8 | 2.53 | 1.53 | 76.0 | 2.67 | 1.66 | 75.2 | 2.46 | 1.48 | 81.9 |
| base + rect | 2.46 | 1.64 | 95.8 | 2.32 | 1.63 | 73.8 | 3.14 | 1.70 | 79.3 | 2.54 | 1.68 | 81.4 |
| Base + rect + order + $\lambda$ | 2.55 | 1.83 | 94.2 | 2.31 | 1.54 | 89.4 | 3.19 | 1.71 | 91.0 | 2.57 | 1.70 | 91.2 |
| Base + rect + optim + $\lambda$ | 2.40 | 1.18 | 96.8 | 2.35 | 1.28 | 97.8 | 3.19 | 1.69 | 97.2 | 2.55 | 1.40 | 97.4 |
| Base + rect + order | 2.54 | 1.84 | 93.7 | 2.33 | 1.25 | 87.2 | 3.15 | 1.69 | 86.9 | 2.57 | 1.58 | 89.0 |
| Base + rect + optim | 2.40 | 1.18 | 96.3 | 2.38 | 1.28 | 94.1 | 3.15 | 1.68 | 92.4 | 2.55 | 1.39 | 94.4 |

Figure 5:
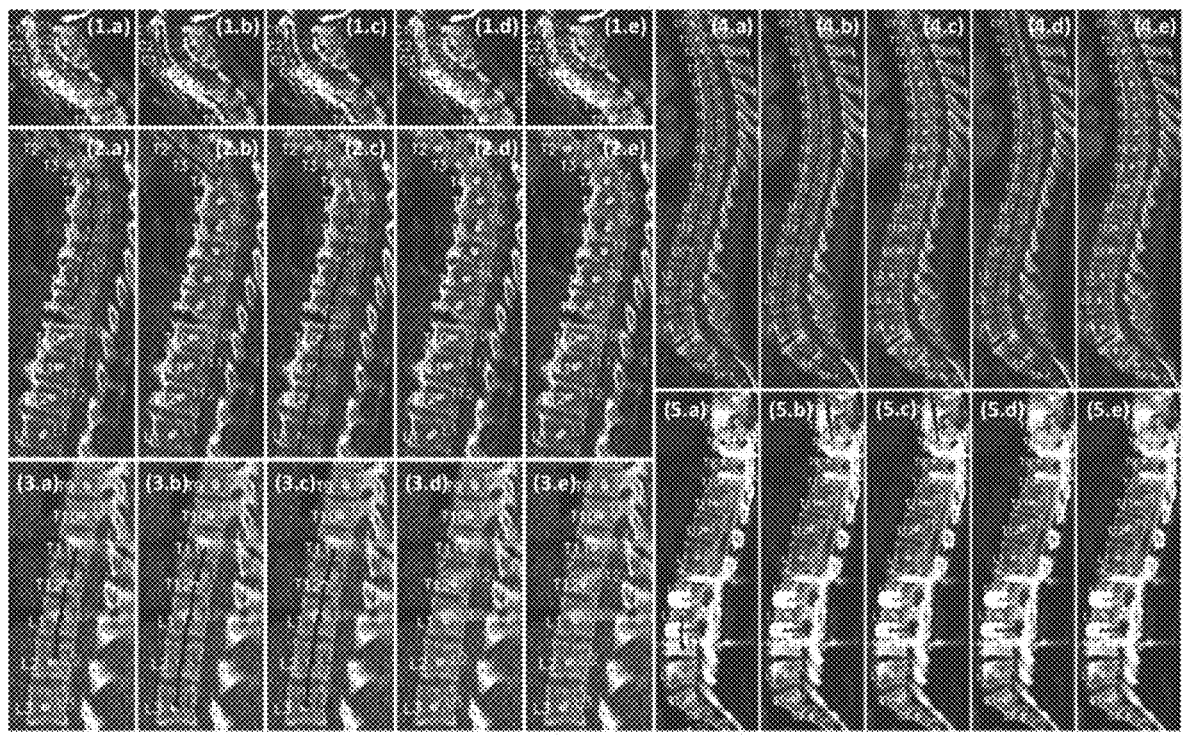
FIG. 5 illustrates comparison of vertebra localization and identification results of five datasets processed by four existing methods and the method consistent with embodiments of the present disclosure.
Figure 7:
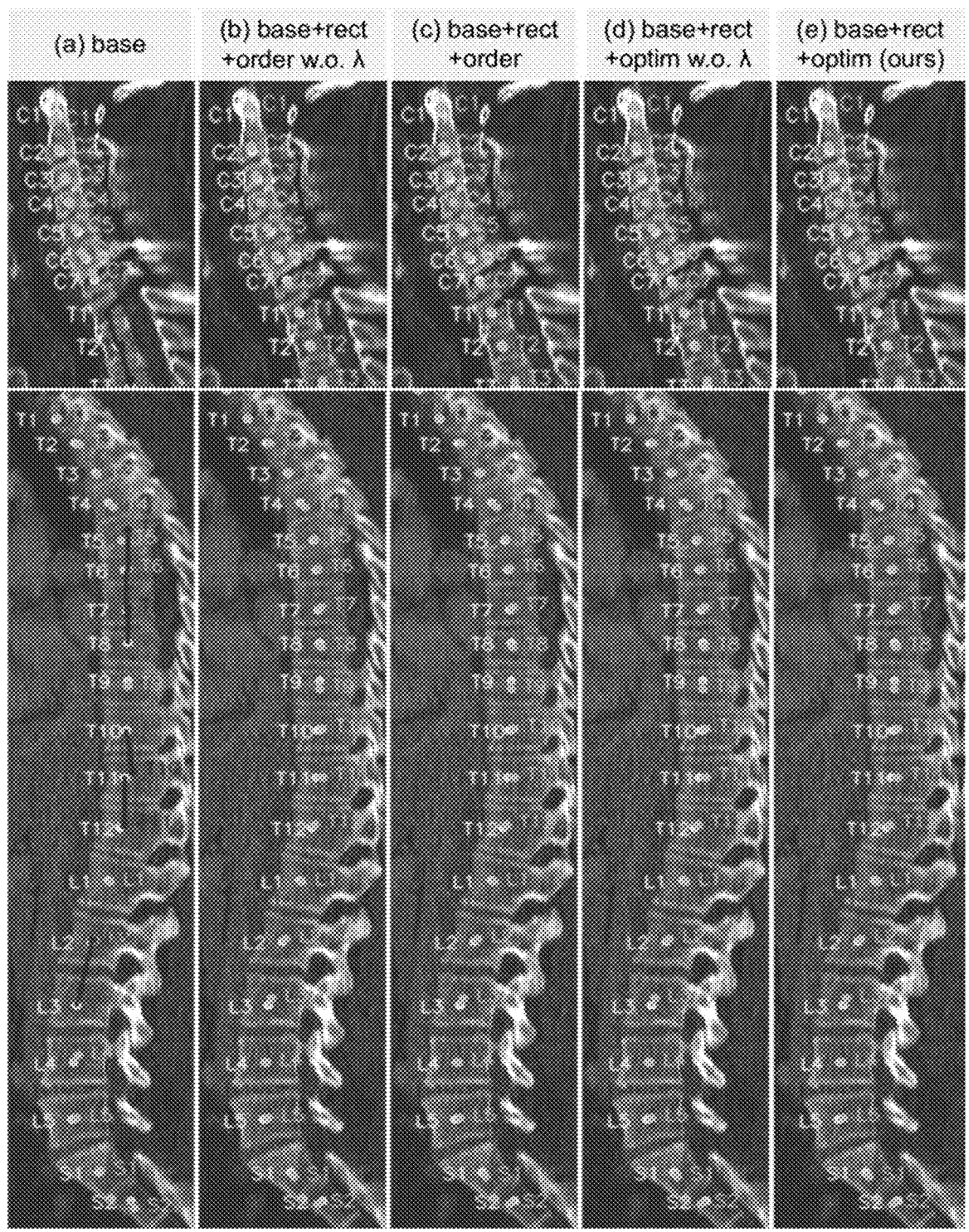
FIG. 7 illustrates comparison of vertebra localization and identification results of five datasets processed by four existing methods and the method consistent with embodiments of the present disclosure.
Figure 8:
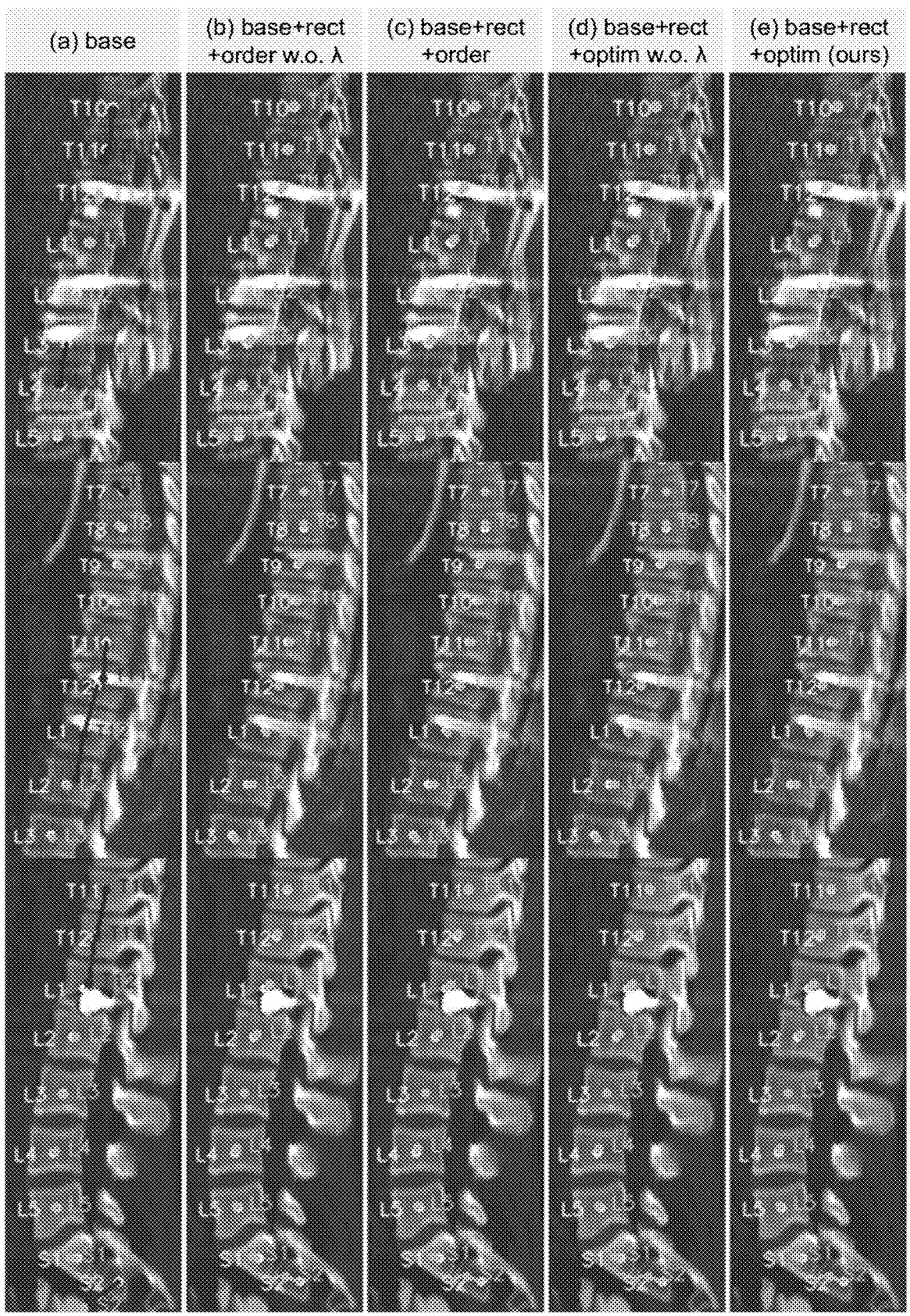
FIG. 8 illustrates comparison of vertebra localization and identification results of five datasets processed by four existing methods and the method consistent with embodiments of the present disclosure.
Figure 9:
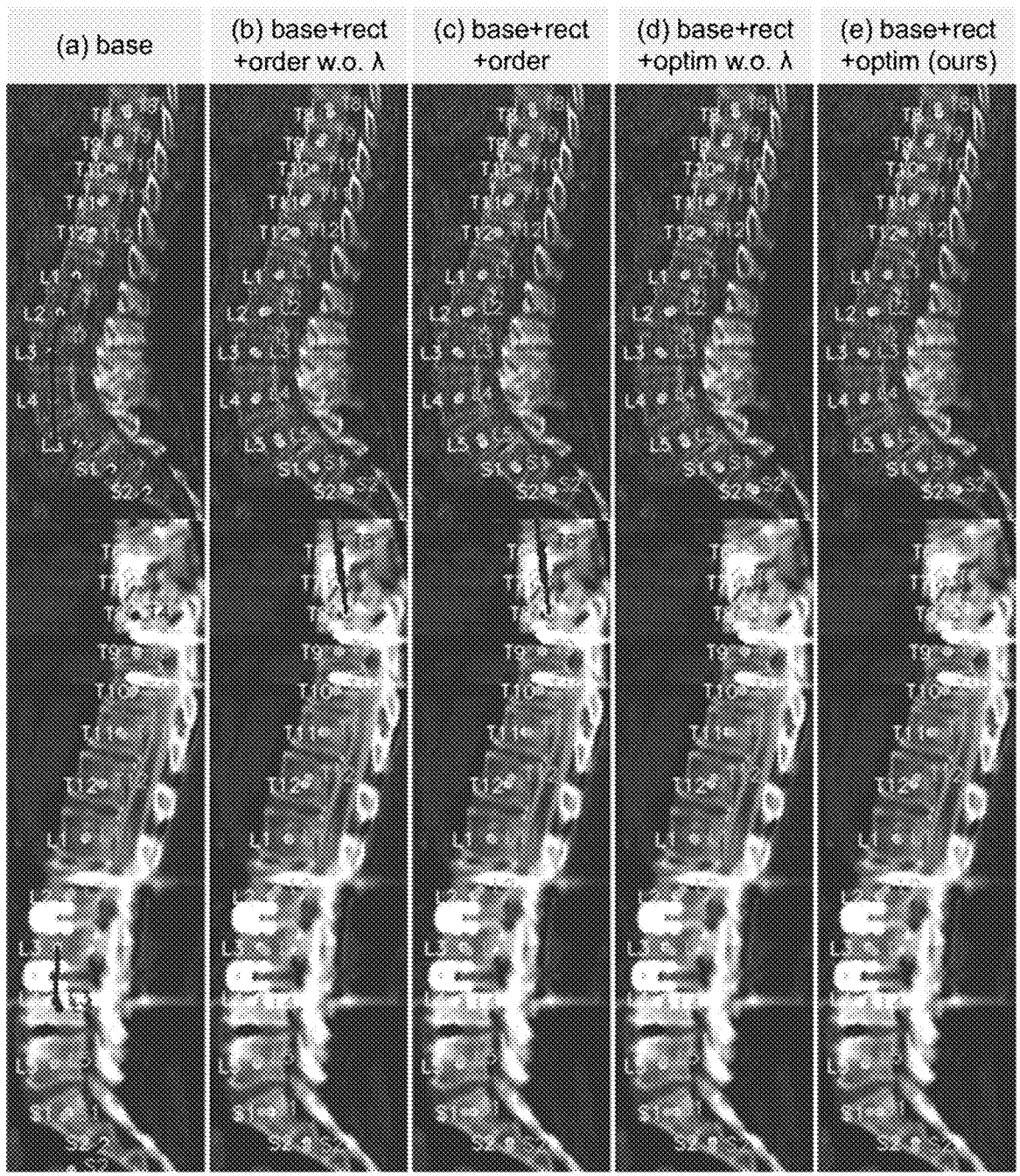
FIG. 9 illustrates comparison of vertebra localization and identification results of five datasets processed by four existing methods and the method consistent with embodiments of the present disclosure.

FIG. 5 illustrates comparison of vertebra localization and identification results of five datasets (1-5) processed by four existing methods (a-d) and the method (e) consistent with embodiments of the present disclosure. The dataset 1 includes CT images in the cervical region. The datasets 2-4 includes CT images in the thoracic region and the lumbar region. The dataset 5 includes CT images with metal implants. The methods include: (a) base, (b) base+rect+order, (c) base+rect+order, (d) base+rect+optim, (e) base+rect+optim+$\lambda$ (present disclosure). The ground-truth vertebra centers are marked by dots and labels on a left side of spine in the CT images. The vertebra centers detected by the method consistent with the embodiments of the present disclosure are marked by dots and labels on a right side of the spine in the CT images. A line is drawn between the ground-truth and the detected centers of the same vertebra for better visualization of the localization error. Similarly, additional examples are shown in FIGS. 7-9.

The purpose of the spine rectification is to enable applying the anatomical constraints in the downstream processing. Thus, employing the spine rectification without imposing the anatomical constraints does not bring any performance gain, as shown by the comparison between base model and base+rect model. By imposing an effective/meaningful constraint of the vertebra order, base+rect+order model ensures physically plausible results and significantly improves the identification rate over base+rect model from 81.4% to 91.2%. By employing the anatomically-constrained optimization, base+rect+optim model is able to regulate the distance between predicted vertebrae while preserving the physically plausible vertebra order. As a result, the identification rate is further improved from 91.2% to 97.4%. It is also observed that while the overall identification rate improves significantly, the identification rate in the cervical region is consistently high using different methods. This is because the cervical vertebrae have a more distinct appearance and can be reliably recognized.

The vertebra weights $\lambda$ also plays an important role by encouraging the optimization to focus more on the vertebrae that can be reliably detected by the key point detection model. To analyze the contribution of the vertebra weights, an experiment is conducted to compare the performances of base+rect+order model and the disclosed method with and without using vertebra weights $\lambda$. As summarized in Table 1, employing vertebra weights $\lambda$ leads to improved performance on both base+rect+order model and the disclosed method. In particular, the overall identification rate is improved from 89.0% and 94.4% to 91.2% and 97.4% on the two methods, respectively. The mean error is not affected much by employing the vertebra weights $\lambda$, which suggests that the vertebra weights $\lambda$ have little effect on the accuracy of correctly identified vertebrae.

Figure 6:
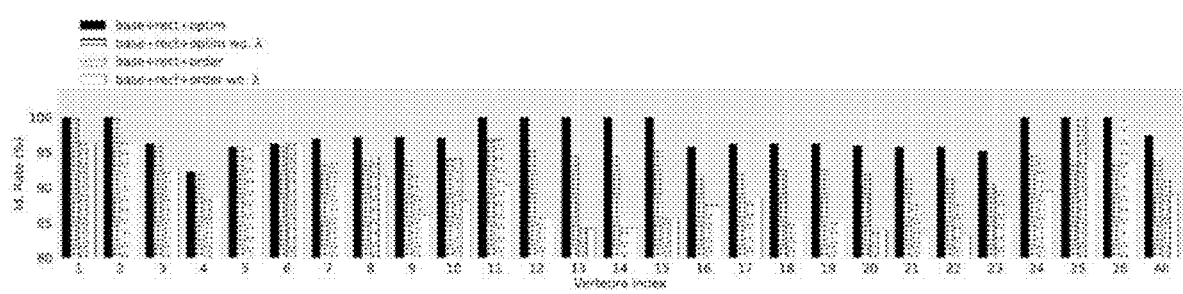
FIG. 6 illustrates comparison of identification rates for each of 26 vertebrae of various alternative methods consistent with embodiments of the present disclosure.

FIG. 6 illustrates comparison of identification rates for each of 26 vertebrae of various alternative methods consistent with embodiments of the present disclosure. As shown in FIG. 6, the disclosed method outperforms the three alternative models for each and every vertebra.

Figure 10:
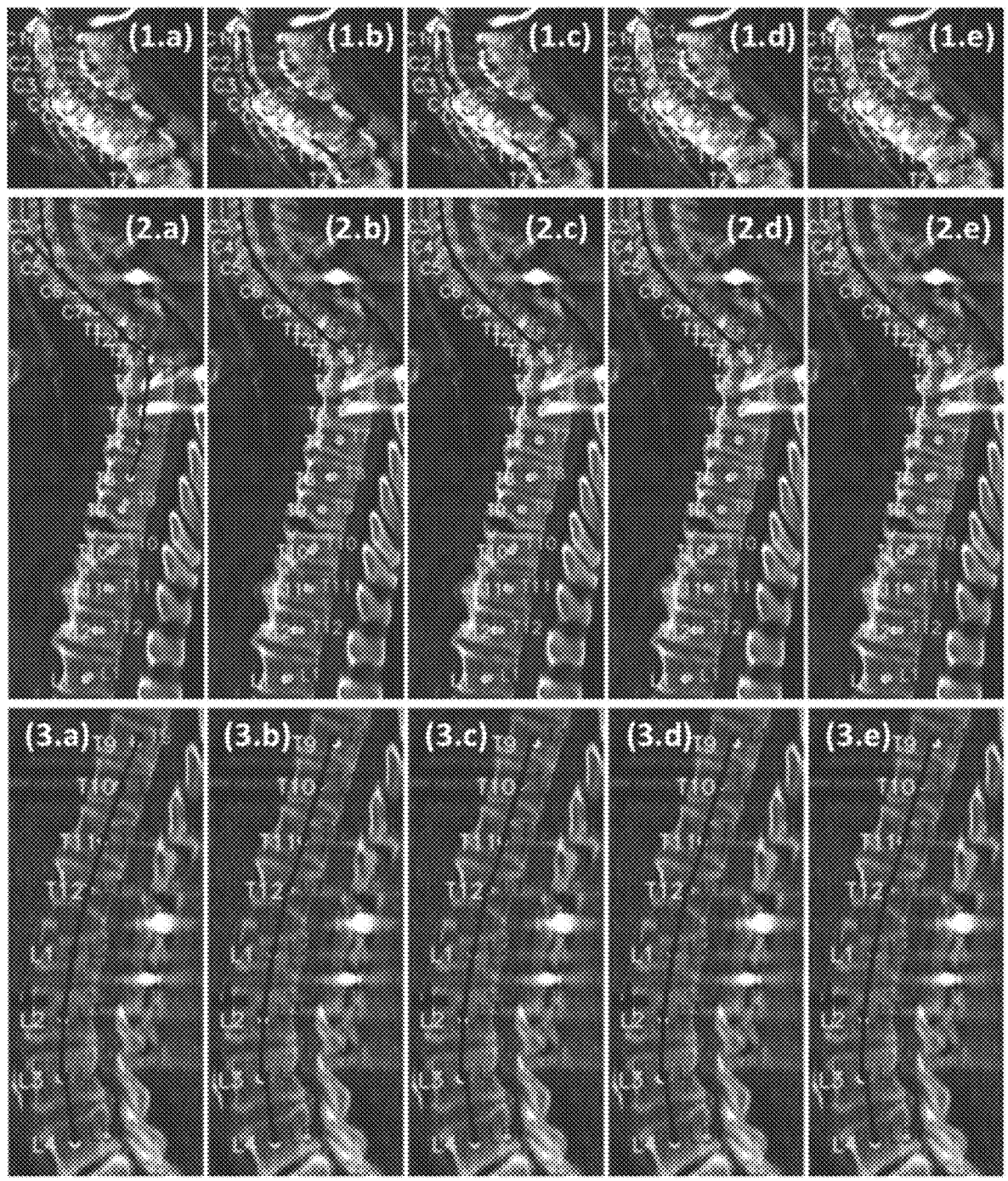
FIG. 10 illustrates incorrectly localized and incorrectly identified vertebrae of three datasets processed by four existing methods and the method consistent with embodiments of the present disclosure.

FIG. 10 illustrates incorrectly localized and incorrectly identified vertebrae of three datasets processed by four existing methods (a-d) and the method (e) consistent with embodiments of the present disclosure. As shown in FIG. 10, three failure cases (1-3) are illustrated. Extreme pathology and/or low image quality may degrade the performance. In particular, the first failure case has severe vertebral compression factures, which significantly reduces the height of the vertebrae as well as the space margins between them. The second failure case has low imaging quality, making it difficult to differentiate the boundary between vertebrae. Consequently, missed detection and false positive results are observed in the above two cases, respectively. In the third case, the vertebra centers are correctly located but labels are off by one. The underlying cause of the third failure case is the lack of distinct vertebrae that can be reliably recognized. In particular, the more distinct L5 and sacrum vertebrae are not in the field of view. The imaging appearance of T12 vertebra (i.e., the lowest vertebra with rib) is affected by the metal implant. The analysis of the failure cases shows that severe pathologies and extreme imaging conditions may still negatively impact the model's performance on robustness.

The vertebra localization and identification method provided by the embodiments of the present disclosure is highly robust and accurate. The thorough evaluations based on the publicly available benchmarks demonstrate that by rectifying the spine (via converting and effectively simplifying 3-D vertebra activation maps into 1-D vertebra activation signals) and jointly localizing all vertebrae following the anatomical constraint, the disclosed method outperforms the existing methods by significantly large quantitative margins. Further, the ablation study validates the effectiveness of each algorithm component.

Figure 11:
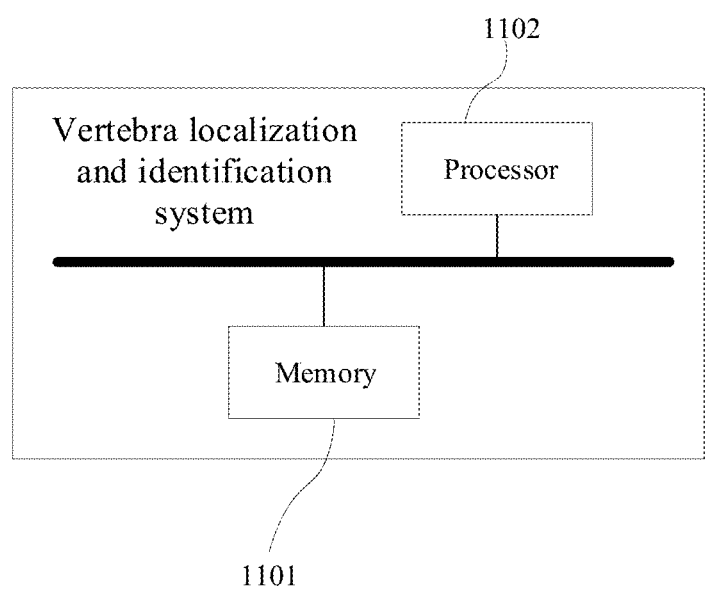
FIG. 11 illustrates a structural diagram of an exemplary device for vertebra localization and identification consistent with embodiments of the present disclosure.

FIG. 11 illustrates a structural diagram of an exemplary device for vertebra localization and identification consistent with embodiments of the present disclosure. Referring to FIG. 11, the present disclosure provides a vertebra localization and identification device. The vertebra localization and identification device performs the disclosed vertebra localization and identification method. Specifically, the vertebra localization and identification device includes a memory 1101 storing a computer program and a processor 1102 configured to execute the computer program stored in the memory 1101 to perform: receiving one or more images of vertebrae of a spine, applying a machine learning model on the one or more images to generate 3-D vertebra activation maps $\{G_v\}$ of detected vertebra centers, performing a spine rectification process on the 3-D vertebra activation maps $\{G_v\}$ to convert each 3-D vertebra activation map $G_v$ into a corresponding one-dimensional (1-D) vertebra activation signal $Q_v$; performing an anatomically-constrained optimization process on each 1-D vertebra activation signal $Q_v$ to localize and identify each vertebra center in the one or more images; and outputting the one or more images, where on each of the one or more outputted images, a location k and an identification $v_l$ of each vertebra center are specified, wherein $v_l \in [1, 26]$.

In some embodiments, the machine learning model is a key point detection model that is trained using U-Net as a backbone network to produce the 3-D activation maps $\{G_v\}$, where $G_v \in \mathbb{R}^{W \times H \times L}$, and $v \in \{1, 2, \ldots, 26\}$, W×H×L is a size of the one or more images, and $\mathbb{R}$ is a mathematical expression of real numbers.

In some embodiments, when performing the spine rectification process on the 3-D vertebra activation maps $\{G_v\}$ to convert each 3-D vertebra activation map $G_v$ into the corresponding 1-D vertebra activation signal $Q_v$, the processor 1102 is configured to combine the 3-D vertebra activation maps $\{G_v\}$ into one combined activation map $\hat{G}$, where $\hat{G} = \Sigma_{v=1}^{26} G_v$; extract a spine centerline s(t) based on the combined activation map $\hat{G}$, where s(t)=(x(t), y(t), z(t)), x(t), y(t), z(t) are x, y, z coordinates of the spine centerline s(t), and t is arc-length parameterization including a distance from a starting point of the spine centerline s(t); and aggregate each 3-D vertebra activation map $G_v$ along the spine centerline s(t) to produce the 1-D vertebra activation signal $Q_v$, where $Q_v(z) = \Sigma_{x,y} G'_v(x, y, z)$.

In some embodiments, when aggregating each 3-D vertebra activation map $G_v$ along the spine centerline s(t) to produce the 1-D vertebra activation signal $Q_v$, the processor 1102 is configured to calculate a moving local coordinate system $\langle e_1(t), e_2(t), e_3(t) \rangle$ along the spine centerline s(t), where $e_3(t)$ is a tangent vector of the spine centerline s(t), $e_2(t)$ is a unit vector in a normal plane of the spine centerline s(t) with a minimum angle toy-axis of the one or more images, and $e_1(t)$ is a cross product of $e_2(t)$ and $e_3(t)$, warp the 3-D vertebra activation maps $\{G_v\}$ and the combined activation map $\hat{G}$ to produce spine rectified 3-D vertebra activation maps $\{G'_v\}$ and spine rectified combined activation map $\hat{G}'$, where $G'_v(x, y, z) = G_v(s(z) + e_1(x) + e_2(y))$, and $G_v(s(z) + e_1(x) + e_2(y))$ denotes linear interpolation of $G_v$ at given (x, y, z) coordinate, x-axis aligns with an anterior direction of each vertebra, y-axis aligns with a right direction of each vertebra, and z-axis aligns with the spine centerline; and process the spine rectified activation maps $\{G'_v\}$ and the spine rectified combined activation map $\hat{G}'$ to produce the 1-D vertebra activation signals $\{Q_v\}$ and $\hat{Q}$, respectively, where $Q_v(z) = \Sigma_{x,y} G'_v(x, y, z)$.

In some embodiments, when performing the anatomically-constrained optimization process on each 1-D vertebra activation signal $Q_v$ to localize and identify each vertebra center in the one or more images, the processor 1102 is configured to determine a parameter ($v_l$, k) for each 1-D vertebra activation signal $Q_v$ by minimizing an energy function $\mathcal{L}(v_l, k)$, wherein $\mathcal{L}(v_l, k) = -\Sigma_{i=0}^{N-1} \lambda_{v_l i} Q_{v_l+i}(k_i) + \Sigma_{i=2}^{N-2} R(k_i - k_{i-1}, k_{i+1} - k_i)$, $v_l$ is a lowest index of an N number of detected vertebrae, $v_l \in [1,26]$, k denotes vertebra centers and $k = \{k_i\}_{i \in [0, N-1]}$, i is the vertebra's index relative to $v_l$, $k_i$ is a location of the vertebra with absolute index $v_l + i$, $Q_{v_l+i}(k_i)$ is an activation value of the vertebra with the absolute index $v_l + i$, $R(k_i - k_{i-1}, k_{i+1} - k_i)$ is a regularization term that encourages distances between neighboring vertebrae to be similar and $$R(k_i - k_{i-1}, k_{i+1} - k_i) = \exp\left(\max\left(\frac{k_i - k_{i-1}}{k_{i+1} - k_i}, \frac{k_{i+1} - k_i}{k_i - k_{i-1}}\right)\right),$$

and $\lambda_v$ is weights of the vertebrae and $$\lambda_v = \begin{cases} 1, & v \in \{3, 4, \ldots, 24\} \\ 2, & v \in \{1, 2, 25, 26\} \end{cases}.$$

In some embodiments, when determining the parameter ($v_l$, k) for each 1-D vertebra activation signal $Q_v$ by minimizing the energy function $\mathcal{L}(v_l, k)$, the processor 1102 is configured to initialize the parameter ($v_l$, k); perform an offset operation to determine $v_l$; perform a fine-tune operation to determine k; perform an expansion operation to determine a location of a missing vertebra center; and iteratively repeat the offset operation, the fine-tune operation, and the expansion operation until convergence occurs.

In some embodiments, when initializing the parameter ($v_l$, k), the processor 1102 is configured to initialize $v_l$ to 1 and k to coordinates of local maxima of $\hat{Q}$ sequentially, wherein $k_{i+1} > k_i$, $k_i \in [0, L]$, and L is a total length of the spine.

In some embodiments, when performing the offset operation to determine $v_l$, the processor 1102 is configured to perform the offset operation to optimize $v_l$ via an exhaustive search $$v_l \leftarrow \underset{v_l}{\arg\min} \mathcal{L}(v_l, k).$$

In some embodiments, when performing the fine-tune operation to determine k, the processor 1102 is configured to perform the fine-tune operation to optimize $\{k_v\}$ via a Hill Climbing optimization process $$k \leftarrow \underset{k}{\arg\min} \mathcal{L}(v_l, k).$$

In some embodiments, when performing the expansion operation to determine the location of the potential missing vertebra center, the processor 1102 is configured to perform the expansion operation by inserting a new vertebra center at an insertion location u to k between $$(u, u+1) \text{ via calculating } k \leftarrow E(k, u) = \begin{cases} k_i & \text{if } i \leq u \\ (k_i + k_{i+1})/2 & \text{if } i = u + 1. \\ k_{i+1} & \text{if } i > u \end{cases}$$

In some embodiments, the insertion location u is searched by minimizing an energy function $\mathcal{L}(v_l, E(k, u))$, wherein $$u = \arg \underset{u \in [0, N-2]}{\min} \mathcal{L}(v_l, E(k, u)).$$

In some embodiments, the identification of each vertebra center on the one or more outputted images is specified by labelling seven cervical vertebrae as C1-C7; twelve thoracic vertebrae as T1-T12; five lumbar vertebrae as L1-L5; and two sacrum vertebrae as S1-S2.

The memory 1101 may include volatile memory such as random-access memory (RAM), and non-volatile memory such as flash memory, hard disk drive (HDD), or solid-state drive (SSD). The memory 1101 may also include combinations of various above-described memories. The processor 1102 may include a central processing unit (CPU), an embedded processor, a microcontroller, and a programmable device such as an application-specific integrated circuit (ASIC), a field programmable gate array (FPGA), and a programmable logic array (PLD), etc.

The vertebra localization and identification device provided by the embodiments of the present disclosure is highly robust and accurate. The thorough evaluations based on the publicly available benchmarks demonstrate that by rectifying the spine (via converting and effectively simplifying 3-D detection activation maps into 1-D detection signals) and jointly localizing all vertebrae following the anatomical constraint, the disclosed device outperforms the existing methods by significantly large quantitative margins.

The present disclosure also provides a computer-readable storage medium storing a computer program. The computer program may be loaded to a computer or a processor of a programmable data processing device, such that the computer program is executed by the computer or the processor of the programmable data processing device to implement the disclosed method.

Although the principles and implementations of the present disclosure are described by using specific embodiments in the specification, the foregoing descriptions of the embodiments are only intended to help understand the method and core idea of the method of the present disclosure. Meanwhile, a person of ordinary skill in the art may make modifications to the specific implementations and application range according to the idea of the present disclosure. In conclusion, the content of the specification should not be construed as a limitation to the present disclosure.

What is claimed is:

1. A vertebra localization and identification method, comprising:
  receiving one or more images of vertebrae of a spine;
  applying a machine learning model on the one or more images to generate three-dimensional (3-D) vertebra activation maps $\{G_v\}$ of detected vertebra centers;
  performing a spine rectification process on the 3-D vertebra activation maps $\{G_v\}$ to convert each 3-D vertebra activation map $G_v$ into a corresponding one-dimensional (1-D) vertebra activation signal $Q_v$;
  performing an anatomically-constrained optimization process on each 1-D vertebra activation signal $Q_v$ to localize and identify each vertebra center in the one or more images; and
  outputting the one or more images, wherein on each of the one or more outputted images, a location k and an identification $v_I$ of each vertebra center are specified, wherein $v_I \in [1, 26]$.

2. The method according to claim 1, wherein:
  the machine learning model is a key point detection model that is trained using U-Net as a backbone network to produce the 3-D vertebra activation maps $\{G_v\}$, wherein $G_v \in \mathbb{R}^{W \times H \times L}$, $v \in \{1, 2, \ldots, 26\}$, W×H×L is a size of the one or more images, and $\mathbb{R}$ is a mathematical expression of real numbers.

3. The method according to claim 1, wherein performing the spine rectification process on the 3-D vertebra activation maps $\{G_v\}$ to convert each 3-D vertebra activation map $G_v$ into the corresponding 1-D vertebra activation signal $Q_v$ includes:
  combining the 3-D vertebra activation maps $\{G_v\}$ into one combined activation map $\hat{G}$, wherein $\hat{G} = \Sigma_{v=1}^{26} G_v$;
  extracting a spine centerline s(t) based on the combined activation map $\hat{G}$, wherein s(t)=(x(t), y(t), z(t)), x(t), y(t), z(t) are x, y, z coordinates of the spine centerline s(t), and t is arc-length parameterization including a distance from a starting point of the spine centerline s(t); and
  aggregating each 3-D vertebra activation map $G_v$ along the spine centerline s(t) to produce the 1-D vertebra activation signal $Q_v$, wherein $Q_v(z) = \Sigma_{x,y} G'_v(x, y, z)$.

4. The method according to claim 3, wherein aggregating each 3-D vertebra activation map $G_v$ along the spine centerline s(t) to produce the 1-D vertebra activation signal $Q_v$ includes:
  calculating a moving local coordinate system $\langle e_1(t), e_2(t), e_3(t) \rangle$ along the spine centerline s(t), wherein $e_3(t)$ is a tangent vector of the spine centerline s(t), $e_2(t)$ is a unit vector in a normal plane of the spine centerline s(t) with a minimum angle toy-axis of the one or more images, and $e_1(t)$ is a cross product of $e_2(t)$ and $e_3(t)$;
  warping the 3-D vertebra activation maps $\{G_v\}$ and the combined activation map $\hat{G}$ to produce spine rectified 3-D vertebra activation maps $\{G'_v\}$ and spine rectified combined activation map $\hat{G}'$, wherein $G'_v(x, y, z) = G_v(s(z)+e_1(x)+e_2(y))$, $G_v(s(z)+e_1(x)+e_2(y))$ denotes linear interpolation of $G_v$ at given (x, y, z) coordinate, x-axis aligns with an anterior direction of each vertebra, y-axis aligns with a right direction of each vertebra, and z-axis aligns with the spine centerline; and
  processing the spine rectified activation maps $\{G'_v\}$ and the spine rectified combined activation map $\hat{G}'$ to produce the 1-D vertebra activation signals $\{Q_v\}$ and $\hat{Q}$, respectively, wherein $Q_v(z) = \Sigma_{x, y} G'_v(x, y, z)$.

5. The method according to claim 1, wherein performing the anatomically-constrained optimization process on each 1-D vertebra activation signal $Q_v$ to localize and identify each vertebra center in the one or more images includes:
  determining a parameter $(v_I, k)$ for each 1-D vertebra activation signal $Q_v$ by minimizing an energy function $\mathcal{L}(v_I, k)$, wherein $\mathcal{L}(v_I, k) = -\Sigma_{i=0}^{N-1} \lambda_{v_I+i} Q_{v_I+i}(k_i) + \Sigma_{i=2}^{N-2} R(k_i - k_{i-1}, k_{i+1} - k_i)$, $v_I$ is a lowest index of an N number of detected vertebrae, $v_I \in [1,26]$, k denotes vertebra centers and $k = \{k_i\}_{i \in [0, N-1]}$, i is the vertebra's index relative to $v_I$, $k_i$ is a location of the vertebra with absolute index $v_I+i$, $Q_{v_I+i}(k_i)$ is an activation value of the vertebra with the absolute index $v_I+i$, $R(k_i - k_{i-1}, k_{i+1} - k_i)$ is a regularization term that encourages distances between neighboring vertebrae to be similar and $$R(k_i - k_{i-1}, k_{i+1} - k_i) = \exp\left(\max\left(\frac{k_i - k_{i-1}}{k_{i+1} - k_i}, \frac{k_{i+1} - k_i}{k_i - k_{i-1}}\right)\right),$$

and $\lambda_v$ is weights of the vertebrae and $$\lambda_v = \begin{cases} 1, & v \in \{3, 4, \ldots, 24\} \\ 2, & v \in \{1, 2, 25, 26\} \end{cases}.$$

6. The method according to claim 5, wherein determining the parameter $(v_I, k)$ for each 1-D vertebra activation signal $Q_v$ by minimizing the energy function $\mathcal{L}(v_I, k)$ includes:
  initializing the parameter $(v_I, k)$;
  performing an offset operation to determine $v_I$;
  performing a fine-tune operation to determine k;

performing an expansion operation to determine a location of a missing vertebra center; and
iteratively repeating the offset operation, the fine-tune operation, and the expansion operation until convergence occurs.

7. The method according to claim 6, wherein initializing the parameter ($v_l$, k) includes:
initializing $v_l$ to 1 and k to coordinates of local maxima of $\hat{Q}$ sequentially, wherein $k_{i+1} > k_i$, $k_i \in [0, L]$, and L is a total length of the spine.

8. The method according to claim 6, wherein performing the offset operation to determine $v_l$ includes:
performing the offset operation to optimize $v_l$ via an exhaustive search $$v_l \leftarrow \operatorname*{argmin}_{v_l} \mathcal{L}(v_l, k).$$

9. The method according to claim 6, wherein performing the fine-tune operation to determine k includes:
performing the fine-tune operation to optimize $\{k_v\}$ via a Hill Climbing optimization process $$k \leftarrow \operatorname*{argmin}_{k} \mathcal{L}(v_l, k).$$

10. The method according to claim 6, wherein performing the expansion operation to determine the location of the potential missing vertebra center includes:
performing the expansion operation by inserting a new vertebra center at an insertion location u to k between (u, u+1) via calculating $$k \leftarrow E(k, u) = \begin{cases} k_i & \text{if } i \leq u \\ (k_i + k_{i+1})/2 & \text{if } i = u+1 \\ k_{i+1} & \text{if } i > u \end{cases}.$$

11. The method according to claim 10, wherein:
the insertion location u is searched by minimizing an energy function $\mathcal{L}(v_l, E(k, u))$, wherein $$u = \arg\min_{u \in [0, N-2]} \mathcal{L}(v_l, E(k, u)).$$

12. The method according to claim 1, wherein the identification of each vertebra center on the one or more outputted images is specified by labelling seven cervical vertebrae as C1-C7; twelve thoracic vertebrae as T1-T12; five lumbar vertebrae as L1-L5; and two sacrum vertebrae as S1-S2.

13. A vertebra localization and identification device, comprising:
a memory storing a computer program; and
a processor configured to execute the computer program stored in the memory to:
receive one or more images of vertebrae of a spine;
apply a machine learning model on the one or more images to generate three-dimensional (3-D) vertebra activation maps $\{G_v\}$ of detected vertebra centers;
perform a spine rectification process on the 3-D vertebra activation maps $\{G_v\}$ to convert each 3-D vertebra activation map $G_v$ into a corresponding one-dimensional (1-D) vertebra activation signal $Q_v$;
perform an anatomically-constrained optimization process on each 1-D vertebra activation signal $Q_v$ to localize and identify each vertebra center in the one or more images; and
output the one or more images, wherein on each of the one or more outputted images, a location k and an identification $v_l$ of each vertebra center are specified, wherein $v_l \in [1, 26]$.

14. The device according to claim 13, wherein:
the machine learning model is a key point localization model that is trained using U-Net as a backbone network to produce the 3-D vertebra activation maps $\{G_v\}$, wherein $G_v \in \mathbb{R}^{W \times H \times L}$, $v \in \{1, 2, \ldots, 26\}$, W×H×L is a size of the one or more images, and $\mathbb{R}$ is a mathematical expression of real numbers.

15. The device according to claim 13, wherein when performing the spine rectification process on the 3-D vertebra activation maps $\{G_v\}$ to convert each 3-D vertebra activation map $G_v$ into the corresponding 1-D vertebra activation signal $Q_v$, the processor is configured to:
combine the 3-D vertebra activation maps $\{G_v\}$ into one combined activation map $\hat{G}$, wherein $\hat{G} = \Sigma_{v=1}^{26} G_v$;
extract a spine centerline s(t) based on the combined activation map $\hat{G}$, wherein s(t)=(x(t), y(t), z(t)), x(t), y(t), z(t) are x, y, z coordinates of the spine centerline s(t), and t is arc-length parameterization including a distance from a starting point of the spine centerline s(t); and
aggregate each 3-D vertebra activation map $G_v$ along the spine centerline s(t) to produce the 1-D vertebra activation signal $Q_v$, wherein $Q_v(z) = \Sigma_{x,y} G'_v(x, y, z)$.

16. The device according to claim 15, wherein when aggregating each 3-D vertebra activation map $G_v$ along the spine centerline s(t) to produce the 1-D vertebra activation signal $Q_v$, the processor is configured to:
calculate a moving local coordinate system ($e_1(t)$, $e_2(t)$, $e_3(t)$) along the spine centerline s(t), wherein $e_3(t)$ is a tangent vector of the spine centerline s(t), $e_2(t)$ is a unit vector in a normal plane of the spine centerline s(t) with a minimum angle toy-axis of the one or more images, and $e_1(t)$ is a cross product of $e_2(t)$ and $e_3(t)$;
warp the 3-D vertebra activation maps $\{G_v\}$ and the combined activation map $\hat{G}$ to produce spine rectified 3-D vertebra activation maps $\{G'_v\}$ and spine rectified combined activation map $\hat{G}'$, wherein $\hat{G}'_v(x, y, z) = G_v(s(z) + e_1(x) + e_2(y))$, $G_v(s(z) + e_1(x) + e_2(y))$ denotes linear interpolation of $G_v$ at given (x, y, z) coordinate, x-axis aligns with an anterior direction of each vertebra, y-axis aligns with a right direction of each vertebra, and z-axis aligns with the spine centerline; and
process the spine rectified activation maps $\{G'_v\}$ and the spine rectified combined activation map $\hat{G}'$ to produce the 1-D vertebra activation signals $\{Q_v\}$ and $\hat{Q}$, respectively, wherein $Q_v(z) = \Sigma_{x,y} G'_v(x, y, z)$.

17. The device according to claim 13, wherein when performing the anatomically-constrained optimization process on each 1-D vertebra activation signal $Q_v$ to localize and identify each vertebra center in the one or more images, the processor is configured to:
determine a parameter ($v_l$, k) for each 1-D vertebra activation signal $Q_v$ by minimizing an energy function $\mathcal{L}(v_l, k)$, wherein $\mathcal{L}(v_l, k) = -\Sigma_{i=0}^{N-1} \lambda_{v_l+i} Q_{v_l+i}(k_i) + \Sigma_{i=2}^{N-2} R(k_i - k_{i-1}, k_{i+1} - k_i)$, $v_l$ is a lowest index of an N number of detected vertebrae, $v_l \in [1, 26]$, k denotes vertebra centers and $k=\{k_i\}_{i\in[0,N-1]}$, i is the vertebra's index relative to $v_l$, $k_i$ is a location of the vertebra with absolute index $v_l$+i, $Q_{v_l+i}(k_i)$ is an activation value of the vertebra with the absolute index $v_l$+i, $R(k_i-k_{i-1}, k_{i+1}-k_i)$ is a regularization term that encourages distances between neighboring vertebrae to be similar and $$R(k_i - k_{i-1}, k_{i+1} - k_i) = \exp\left(\max\left(\frac{k_i - k_{i-1}}{k_{i+1} - k_i}, \frac{k_{i+1} - k_i}{k_i - k_{i-1}}\right)\right),$$

and $\lambda_v$ is weights of the vertebrae and $$\lambda_v = \begin{cases} 1, & v \in \{3, 4, \ldots, 24\} \\ 2, & v \in \{1, 2, 25, 26\} \end{cases}.$$

18. The device according to claim 17, wherein when determining the parameter ($v_l$, k) for each 1-D vertebra activation signal $Q_v$ by minimizing the energy function $\mathcal{L}(v_l, k)$, the processor is configured to:
 initialize the parameter ($v_l$, k);
 perform an offset operation to determine $v_l$;
 perform a fine-tune operation to determine k;
 perform an expansion operation to determine a location of a missing vertebra center; and
 iteratively repeat the offset operation, the fine-tune operation, and the expansion operation until convergence occurs.

19. A non-transitory computer-readable storage medium storing a computer program, when being executed by a processor, the computer program performing:
 receiving one or more images of vertebrae of a spine;
 applying a machine learning model on the one or more images to generate three-dimensional (3-D) vertebra activation maps $\{G_v\}$ of detected vertebra centers;
 performing a spine rectification process on the 3-D vertebra activation maps $\{G_v\}$ to convert each 3-D vertebra activation map $G_v$ into a corresponding one-dimensional (1-D) vertebra activation signal $Q_v$;
 performing an anatomically-constrained optimization process on each 1-D vertebra activation signal $Q_v$ to localize and identify each vertebra center in the one or more images; and
 outputting the one or more images, wherein on each of the one or more outputted images, a location k and an identification $v_l$ of each vertebra center are specified, wherein $v_l \in [1, 26]$.

20. The non-transitory computer-readable storage medium according to claim 19, wherein:
 the machine learning model is a key point detection model that is trained using U-Net as a backbone network to produce the 3-D vertebra activation maps $\{G_v\}$, wherein $G_v \in \mathcal{L}^{W \times H \times L}$, $v \in \{1, 2, \ldots, 26\}$, W×H×L is a size of the one or more images, and $\mathcal{L}$ is a mathematical expression of real numbers.

* * * * *